(12) United States Patent
Ekwuribe et al.

(10) Patent No.: US 6,903,082 B2
(45) Date of Patent: Jun. 7, 2005

(54) METHODS OF TREATING INFLAMMATORY CONDITIONS OF THE GASTROINTESTINAL TRACT USING 4-APAA AND COMPOSITIONS THEREOF

(75) Inventors: Nnochiri Nkem Ekwuribe, Cary, NC (US); Jennifer A. Riggs-Sauthier, Raleigh, NC (US)

(73) Assignee: Nobex Corporation, Durham, NC (US)

( * ) Notice: Subject to any disclaimer, the term of this patent is extended or adjusted under 35 U.S.C. 154(b) by 110 days.

(21) Appl. No.: 10/444,668

(22) Filed: May 23, 2003

(65) Prior Publication Data

US 2003/0191186 A1 Oct. 9, 2003

Related U.S. Application Data

(62) Division of application No. 09/942,464, filed on Aug. 29, 2001, now Pat. No. 6,583,128.
(60) Provisional application No. 60/228,683, filed on Aug. 29, 2000.

(51) Int. Cl.[7] .............................................. A61K 31/196
(52) U.S. Cl. ...................... 514/162; 514/538; 514/567
(58) Field of Search ................................ 514/162, 567, 514/538, 533

(56) References Cited

U.S. PATENT DOCUMENTS

| | | | |
|---|---|---|---|
| 1,157,169 A | 10/1915 | Mettler | |
| 2,270,676 A | 1/1942 | Behnisch et al. | 260/397.7 |
| 2,314,023 A | 3/1943 | Straub et al. | 260/143 |
| 2,336,275 A | 12/1943 | McNally et al. | 260/199 |
| 2,396,019 A | 3/1946 | Murray | 260/199 |
| 3,244,694 A | 4/1966 | May et al. | 260/187 |
| 3,641,040 A | 2/1972 | Camey et al. | 260/293.72 |
| 3,915,951 A | 10/1975 | Agback et al. | 260/156 |
| 4,189,607 A | 2/1980 | Amano et al. | 562/457 |
| 4,298,595 A | 11/1981 | Parkinson et al. | 424/78 |
| 4,348,399 A | 9/1982 | Shepherd | 424/263 |
| 4,374,932 A | 2/1983 | Pitzele et al. | 521/32 |
| 4,412,992 A | 11/1983 | Chan | 424/226 |
| 4,455,305 A | 6/1984 | Rokos | 424/226 |
| 4,472,433 A | 9/1984 | Ueda et al. | 424/319 |
| 4,493,823 A | 1/1985 | Moller et al. | |
| 4,496,553 A | 1/1985 | Halskov | 514/166 |
| 4,504,494 A | 3/1985 | Grollier et al. | |
| 4,528,367 A | 7/1985 | Agback et al. | 534/599 |
| 4,539,198 A | 9/1985 | Powell et al. | 424/19 |
| 4,540,685 A | 9/1985 | Bauer | 514/162 |
| 4,559,330 A | 12/1985 | Agback et al. | 514/166 |
| 4,591,584 A | 5/1986 | Agback | 514/160 |
| 4,595,699 A | 6/1986 | Terada et al. | 514/570 |

(Continued)

FOREIGN PATENT DOCUMENTS

| | | | | |
|---|---|---|---|---|
| DE | 4121849 A1 | 1/1993 | | C07C/57/38 |
| EP | 0 036 636 A1 | 9/1981 | | |
| EP | 0 036 636 B1 | 9/1981 | | |
| EP | 0094599 A1 | 11/1983 | | A61K/31/195 |
| GB | 2203434 A | 10/1988 | | C07C/107/06 |
| SE | 8606254 A | 10/1986 | | C07C/107/06 |
| WO | WO94/00135 | 1/1994 | | A61K/31/74 |
| WO | WO95/31194 | 11/1995 | | A61K/31/195 |

OTHER PUBLICATIONS

Beilstein Registry No: 926638.
E. Hackmann & P. Ferreira, "Nuovi Azoderivati Solfammidici," *Biol. Chim. Form.*, 114: 501–508.

(Continued)

*Primary Examiner*—Fiona T. Powers
(74) *Attorney, Agent, or Firm*—Moore & Van Allen PLLC; William A. Barrett

(57) ABSTRACT

Compounds are disclosed having the structure of Formula I:

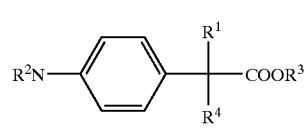

(I)

where $R^1$, $R^3$, and $R^4$ are independently hydrogen or $C_1$ to $C_4$ alkyl, and $R^2$ is:

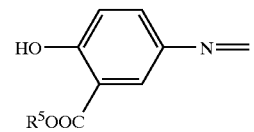

where $R^5$ is selected from the group consisting of hydrogen and $C_1$ to $C_4$ alkyl, or

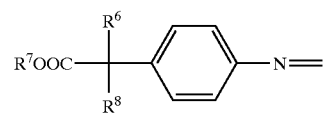

where $R^6$, $R^7$ and $R^8$ are independently hydrogen or $C_1$ to $C_4$ alkyl; or the esters or pharmacologically acceptable salts thereof. Such compounds may be utilized for the prophylaxis or treatment of various diseases, particularly inflammatory conditions of the GI tract.

Methods of treating inflammatory conditions of the GI tract such as inflammatory bowel disease using compounds having the following formula are also disclosed:

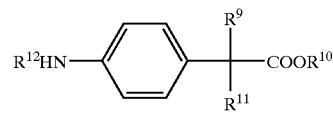

where $R^9$, $R^{10}$ and $R^{11}$ are independently selected from the group consisting of hydrogen and $C_1$ to $C_4$ alkyl, and $R^{12}$ is selected from the group consisting of hydrogen and —C(O)$R^{13}$, where $R^{13}$ is a $C_1$ to $C_6$ alkyl or an aryl group.

16 Claims, 4 Drawing Sheets

U.S. PATENT DOCUMENTS

| | | | | |
|---|---|---|---|---|
| 4,628,083 | A | 12/1986 | Agback | 534/798 |
| 4,632,921 | A | 12/1986 | Bauer | 514/163 |
| 4,657,900 | A | 4/1987 | Powell et al. | 514/166 |
| 4,663,308 | A | 5/1987 | Saffran et al. | 514/3 |
| 4,664,256 | A | 5/1987 | Halskov | 206/213.1 |
| 4,670,112 | A | 6/1987 | Lund | 204/74 |
| 4,699,902 | A | 10/1987 | Bauer | 514/163 |
| 4,720,506 | A | 1/1988 | Munakata et al. | 514/538 |
| 4,725,676 | A | 2/1988 | Agback et al. | 534/853 |
| 4,737,240 | A | 4/1988 | Davis et al. | |
| 4,780,318 | A | 10/1988 | Appelgren et al. | 424/469 |
| 4,788,331 | A | 11/1988 | Sjostrand | 562/453 |
| 4,837,229 | A | 6/1989 | Rokos et al. | 514/517 |
| 4,849,416 | A | 7/1989 | Pendleton et al. | 514/150 |
| 4,873,321 | A | 10/1989 | Omura et al. | |
| 4,880,794 | A | 11/1989 | Halskov | 514/166 |
| 4,889,846 | A | 12/1989 | Crossley | 514/150 |
| 4,904,765 | A | 2/1990 | Derber et al. | |
| 4,911,922 | A | 3/1990 | Masuhara et al. | 424/81 |
| 4,920,206 | A | 4/1990 | Behringer et al. | |
| RE33,239 | E | 6/1990 | Halskov | 206/213.1 |
| 4,933,330 | A | 6/1990 | Jorgensen et al. | 514/159 |
| 4,960,765 | A | 10/1990 | Halskov | 514/166 |
| 4,999,347 | A | 3/1991 | Sorenson | |
| 5,010,069 | A | 4/1991 | Bottom et al. | 514/166 |
| 5,013,727 | A | 5/1991 | Halskov | 514/166 |
| 5,026,560 | A | 6/1991 | Makino et al. | 424/494 |
| 5,037,968 | A | 8/1991 | Simon et al. | |
| 5,041,431 | A | 8/1991 | Halskov | 514/166 |
| 5,082,651 | A | 1/1992 | Healey et al. | 424/45 |
| 5,089,468 | A | 2/1992 | Yoshida et al. | |
| 5,137,916 | A | 8/1992 | Ulrich et al. | |
| 5,244,922 | A | 9/1993 | Burzynski | |
| 5,254,587 | A | 10/1993 | Burzynski | 514/563 |
| 5,272,176 | A | 12/1993 | Ulrich et al. | |
| 5,274,002 | A | 12/1993 | Hawkins | 514/530 |
| 5,330,981 | A | 7/1994 | Rosini et al. | |
| 5,352,681 | A | 10/1994 | Wittebrood et al. | 514/166 |
| 5,378,470 | A | 1/1995 | Lahr | 424/436 |
| 5,391,575 | A | 2/1995 | Burzynski | |
| 5,393,779 | A | 2/1995 | Holloway et al. | 514/539 |
| 5,409,711 | A | 4/1995 | Mapelli et al. | 424/490 |
| 5,434,184 | A | 7/1995 | Holloway et al. | 514/567 |
| 5,476,849 | A | 12/1995 | Ulrich et al. | 514/237.5 |
| 5,480,910 | A | 1/1996 | Holloway et al. | 514/567 |
| 5,484,605 | A | 1/1996 | Scheiffele et al. | 424/451 |
| 5,487,770 | A | 1/1996 | Dyllick-Brenzinger et al. | |
| 5,498,608 | A | 3/1996 | Johnson et al. | 514/150 |
| 5,502,078 | A | 3/1996 | Holloway et al. | 514/567 |
| 5,514,676 | A | 5/1996 | Ulrich et al. | 514/231.2 |
| 5,519,014 | A | 5/1996 | Borody | |
| 5,541,170 | A | 7/1996 | Rhodes et al. | 514/166 |
| 5,541,171 | A | 7/1996 | Rhodes et al. | 514/166 |
| 5,574,050 | A | 11/1996 | Carrell et al. | |
| 5,593,971 | A | 1/1997 | Tschollar et al. | |
| 5,602,183 | A | 2/1997 | Martin et al. | 514/724 |
| 5,629,012 | A | 5/1997 | Halskov | 424/436 |
| 5,629,020 | A | 5/1997 | Leone-Bay et al. | 424/489 |
| 5,631,294 | A | 5/1997 | Kurtz et al. | |
| 5,635,533 | A | 6/1997 | Samid | |
| 5,637,618 | A | 6/1997 | Kurtz et al. | 514/568 |
| 5,646,182 | A | 7/1997 | Burzynski | |
| 5,648,380 | A | 7/1997 | Martin | 514/461 |
| 5,654,333 | A | 8/1997 | Samid | |
| 5,661,179 | A | 8/1997 | Samid | |
| 5,663,208 | A | 9/1997 | Martin | 514/724 |
| 5,667,789 | A | 9/1997 | Collin et al. | |
| 5,668,123 | A | 9/1997 | Martin | 514/166 |
| 5,674,912 | A | 10/1997 | Martin | 514/724 |
| 5,696,243 | A | 12/1997 | Beckmann et al. | |
| 5,703,073 | A | 12/1997 | Garvey et al. | 514/226.5 |
| 5,708,025 | A | 1/1998 | Samid | |
| 5,716,648 | A | 2/1998 | Halskov et al. | 424/682 |
| 5,725,872 | A | 3/1998 | Stamm et al. | 424/435 |
| 5,731,302 | A | 3/1998 | Farolfi et al. | 514/166 |
| 5,739,299 | A | 4/1998 | Hall | |
| 5,747,477 | A | 5/1998 | Carceller et al. | 514/150 |
| 5,747,532 | A | 5/1998 | Lai | 514/491 |
| 5,770,708 | A | 6/1998 | Bermes | |
| 5,817,321 | A | 10/1998 | Alakhov et al. | 424/400 |
| 5,827,332 | A | 10/1998 | Zeidler et al. | |
| 5,840,724 | A | 11/1998 | Fenton et al. | |
| 5,840,966 | A | 11/1998 | Kumarathasan et al. | 562/453 |
| 5,843,994 | A | 12/1998 | Samid | 514/510 |
| 5,852,056 | A | 12/1998 | Samid | |
| 5,861,426 | A | 1/1999 | Del Soldato et al. | |
| 5,866,608 | A | 2/1999 | Kurtz et al. | 514/568 |
| 5,874,479 | A | 2/1999 | Martin | 514/724 |
| 5,877,213 | A | 3/1999 | Samid | 514/568 |
| 5,883,124 | A | 3/1999 | Samid | 514/538 |
| 5,905,073 | A | 5/1999 | Johnson et al. | 514/150 |
| 5,935,601 | A | 8/1999 | Leone-Bay et al. | 424/489 |
| 5,939,455 | A | 8/1999 | Rephaeli | |
| 5,939,456 | A | 8/1999 | Perrine | |
| 5,945,411 | A | 8/1999 | Larson et al. | 514/171 |
| 5,955,472 | A | 9/1999 | Hays et al. | |
| 5,962,710 | A | 10/1999 | Gschneidner et al. | 554/112 |
| 5,973,126 | A | 10/1999 | Ueno et al. | |
| 5,985,927 | A | 11/1999 | Kreutz | 514/568 |
| 6,008,208 | A | 12/1999 | Petrie et al. | |
| 6,008,250 | A | 12/1999 | Kurtz et al. | |
| 6,037,376 | A | 3/2000 | Samid | 514/568 |
| 6,043,233 | A | 3/2000 | Garvey et al. | 514/159 |
| 6,124,504 | A | 9/2000 | Hupperts et al. | 564/415 |
| 6,127,349 | A | 10/2000 | Chasalow | 514/77 |
| 6,183,549 | B1 | 2/2001 | Wight | |
| 6,191,265 | B1 | 2/2001 | Hamprecht | |
| 6,197,341 | B1 | 3/2001 | Friess et al. | |
| 6,225,296 | B1 | 5/2001 | Kapadia | |
| 6,245,735 | B1 | 6/2001 | Pier | 514/2 |
| 6,245,802 | B1 | 6/2001 | Iyengar et al. | |
| 6,277,412 | B1 | 8/2001 | Otterbeck | 424/490 |
| 6,277,836 | B1 | 8/2001 | Borody | 514/159 |
| 6,281,203 | B1 | 8/2001 | Touzan et al. | |
| 6,294,186 | B1 | 9/2001 | Beerse et al. | |
| 6,313,107 | B1 | 11/2001 | Vasudevan et al. | |
| 6,319,951 | B1 | 11/2001 | Chege | |
| 6,326,364 | B1 | 12/2001 | Lin et al. | |
| 6,344,561 | B2 | 2/2002 | Vuligonda | |
| 6,348,497 | B1 | 2/2002 | Billingham | |
| 6,369,261 | B1 | 4/2002 | Johnson et al. | 560/59 |
| 6,375,733 | B1 | 4/2002 | Bindra | |
| 6,380,256 | B1 | 4/2002 | Vasudevan et al. | 514/567 |
| 6,383,471 | B1 | 5/2002 | Chen et al. | 424/45 |
| 6,384,023 | B2 | 5/2002 | Singleton | |
| 6,387,892 | B1 | 5/2002 | Vasudevan et al. | |
| 6,387,952 | B1 | 5/2002 | Mazurek et al. | 514/552 |
| 6,391,832 | B2 | 5/2002 | Lyons et al. | 508/491 |
| 6,399,647 | B2 | 6/2002 | Kalgutkar et al. | |
| 6,403,646 | B1 | 6/2002 | Perlmutter et al. | |
| 6,409,812 | B1 | 6/2002 | Ueno et al. | |
| 6,413,494 | B1 | 7/2002 | Lee et al. | 424/9.1 |
| 6,414,026 | B1 | 7/2002 | Billingham | |
| 6,423,696 | B1 | 7/2002 | Collins et al. | 514/159 |
| 6,426,338 | B1 | 7/2002 | Borody | 514/159 |
| 6,437,104 | B1 | 8/2002 | Nickel et al. | |
| 6,441,221 | B1 | 9/2002 | Shapiro | |
| 6,444,221 | B1 * | 9/2002 | Shapiro | 424/451 |
| 6,458,776 | B1 | 10/2002 | Ekwuribe et al. | |
| 6,479,528 | B1 | 11/2002 | Kuret et al. | |
| 6,488,947 | B1 | 12/2002 | Bekele | |

| | | |
|---|---|---|
| 6,495,552 B2 | 12/2002 | Vasudevan et al. |
| 6,528,076 B2 | 3/2003 | Small et al. |
| 6,541,670 B2 | 4/2003 | Ottosen |
| 6,551,620 B2 | 4/2003 | Otterbeck et al. |
| 6,551,632 B2 | 4/2003 | Borody |
| 6,552,077 B2 | 4/2003 | Cohen |
| 6,566,507 B2 | 5/2003 | Wood et al. |
| 6,573,252 B1 | 6/2003 | Del Soldato |
| 6,583,128 B2 | 6/2003 | Ekwuribe et al. |
| 6,583,273 B1 | 6/2003 | Bacher et al. |
| 6,589,944 B1 | 7/2003 | Rahbar |
| 6,599,748 B1 | 7/2003 | Nakajima et al. |
| 6,602,987 B1 | 8/2003 | Wilchek et al. |
| 6,613,807 B2 | 9/2003 | Uhrich |
| 6,630,463 B2 | 10/2003 | Kikuchi et al. |
| 6,653,352 B2 | 11/2003 | Barr et al. |
| 6,660,283 B2 | 12/2003 | Breton et al. |
| 6,720,344 B2 | 4/2004 | Kerwin et al. |
| 2001/0016586 A1 | 8/2001 | Guitard |
| 2001/0044466 A1 | 11/2001 | Burzynski et al. |
| 2001/0046509 A1 | 11/2001 | Breton et al. |
| 2001/0046979 A1 | 11/2001 | Roselle et al. |
| 2002/0061339 A1 | 5/2002 | Stogniew et al. |
| 2002/0088233 A1 | 7/2002 | Melles |
| 2002/0120008 A1 | 8/2002 | Benzer et al. |
| 2002/0143011 A1 | 10/2002 | Warrellow |
| 2002/0150986 A1 | 10/2002 | Vasudevan et al. |
| 2002/0160986 A1 | 10/2002 | Vasudevan et al. |
| 2002/0183285 A1 | 12/2002 | Vasudevan et al. |
| 2002/0198348 A1 | 12/2002 | Saminathan et al. |
| 2003/0002203 A1 | 1/2003 | Gustafson et al. |
| 2003/0013746 A1 | 1/2003 | Hudson et al. |
| 2003/0017995 A1 | 1/2003 | Khalifah et al. |
| 2003/0018069 A1 | 1/2003 | Faller et al. |
| 2003/0018077 A1 | 1/2003 | Billingham et al. |
| 2003/0077308 A1 | 4/2003 | Rosen |
| 2003/0098243 A1 | 5/2003 | Sanchez-Cano |
| 2003/0108496 A1 | 6/2003 | Yu et al. |
| 2003/0119792 A1 | 6/2003 | Roca |
| 2003/0125306 A1 | 7/2003 | Lan-Hargest et al. |
| 2003/0130300 A1 | 7/2003 | Linz et al. |
| 2003/0133966 A1 | 7/2003 | Syverson et al. |
| 2003/0144276 A1 | 7/2003 | Kikuchi et al. |
| 2003/0152566 A1 | 8/2003 | Schonbeck et al. |
| 2003/0162754 A1 | 8/2003 | Ligon |
| 2003/0166621 A1 | 9/2003 | Kreutz |
| 2003/0171306 A1 | 9/2003 | Davis et al. |
| 2003/0176401 A1 | 9/2003 | Carceller et al. |
| 2003/0176506 A1 | 9/2003 | Dawson et al. |
| 2003/0181492 A1 | 9/2003 | Baynes et al. |
| 2003/0181618 A1 | 9/2003 | Saminathan |
| 2003/0191146 A1 | 10/2003 | Kabbash et al. |
| 2003/0191186 A1 | 10/2003 | Ekwuribe et al. |

OTHER PUBLICATIONS

Frommel et al., "La Paraminobenzolsulfonesuccinylimide, Sulfamide Soluble Neutre et aI Injectable," *Holv. Physiol. Acta*, 3: 261–268 (1945).

Jain et al., "Studies in Sulphanilamides. Part XIII. Reaction with Dicarboxylic Acids. Some New $N^1$–and $N^4$–Acyl adn Heterocyclic Derivatives," *J. Indian Chem. Soc.*, 24: 173–176 (1947).

Kimura et al., "Determination of the Active Moiety of BX661A, a New Therapeutic Agent for Ulcerative Coitis, by Studying Its Therapeutic Effects on Ulcerative Colitis Indeced by Dextran Sulfate Sodium in Rats," *Drug Res.*, 48(II)(11): 1091–1096 (1998).

Nerdel et al., Chemical Abstracts, 55:443F (1961).

Osman et al., "Synthesis of Sulfanilamido–Naphtoquinones as Potential Antiuberculous Agents," *Journal of Pharmaceutical Sciences*, 72(1): 68–71 (1983).

T. Chu & C.S. marvel, "A Proof of the Unsymmetrical Strcuture of the Azoxy Group," *Journal of the American Chemical Society*, 55: 2841–2850 (1993).

International Search Report corresponding to PCT/US01/26697, mailed Jun. 6, 2002.

Partial International Search Report corresponding to PCT/US01/26697, mailed Apr. 4, 2002.

A Proof of the Unsymmetrical Structure of the Azoxy Group, by Tse–Tsing Gnu and C.S. Marvel, *Chemical Laboratory of the University of Illinois*, vol. 55, pp. 2841–2850, Jul. 6, 1933.

Beilstein Search Results, 2272343; Journal; Wittenberg; ZRKOAC; Zh.Russ. Fiz–Khim, O–va; 16; 1884; 590; CHBEAM; Chem.Ber.; 17 Ref. <1884>,432.

* cited by examiner

METHODS OF TREATING INFLAMMATORY CONDITIONS OF THE GASTROINTESTINAL TRACT USING 4-APAA AND COMPOSITIONS THEREOF

RELATED APPLICATIONS

This application is a divisional application of, and claims priority to, U.S. patent application Ser. No. 09/942,464, filed Aug. 29, 2001, issued as U.S. Pat. No. 6,583,128 on Jun. 24, 2003, which claims priority to U.S. Provisional Application No. 60/228,683, filed Aug. 29, 2000, the disclosures of each of which are incorporated herein by reference in their entireties.

FIELD OF THE INVENTION

The present invention relates to immunoregulatory compounds and methods of treating diseases therewith.

BACKGROUND OF THE INVENTION

Many people suffer from inflammatory bowel disease (IBD). IBD is a generic term used to refer to two inflammatory diseases, ulcerative colitis and Crohn's disease. Ulcerative colitis is a chronic inflammatory disease of unknown etiology that affects various portions of the gastrointestinal (GI) tract, particularly the lower GI tract, and more particularly the colon and/or rectum. Crohn's disease is a serious inflammatory disease of the GI tract. It predominates in the small intestine (ileum) and the large intestine (colon). Various medications are being used to treat inflammatory bowel disease.

It is known to use mesalamine, 5-aminosalicylic acid (5-ASA) to treat ulcerative colitis. While mesalamine may be active in treating ulcerative colitis, it may be absorbed as it passes through the GI tract. This absorption may adversely affect the amount of mesalamine that reaches the lower GI tract, particularly the colon and rectum.

Various mesalamine formulations have been introduced in an attempt to protect mesalamine as it passes through the gut and the upper GI tract. One such formulation is a delayed-release formulation that relies on a pH-sensitive coating surrounding the mesalamine. The coating allows the mesalamine to pass through the gut and upper GI tract without being absorbed so that the mesalamine reaches the target (i.e. the lower GI tract, particularly the colon and/or rectum) intact. In another formulation, mesalamine microspheres surround a mesalamine core. This formulation releases mesalamine throughout the GI tract, rather than targeting the colon specifically. It may be difficult to predict the bioavailability of the various mesalamine formulations when administered to a wide variety of individuals. As a result, it may be difficult to determine the proper dosage for a given individual.

It is also known to use sulfasalazine having the following formula to treat ulcerative colitis.

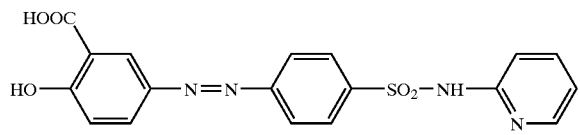

However, sulfasalazine is metabolized in the body to form mesalamine (5-aminosalicylic acid (5-ASA)) and sulfapyridine. Several adverse side affects have been noted from the use of sulfasalazine including nausea, vomiting, abdominal discomfort, and headache to name just a few. These adverse side effects are usually attributed to the activity of sulfapyridine in the GI tract, as well as that absorbed into the system.

U.S. Pat. No. 4,412,992 to Chan proposes mesalamine derivatives. Unlike sulfalazine, the breakdown of these compounds in the intestinal tract may not give rise to undesirable metabolic products. In fact, the non-mesalamine metabolic products may be innocuous.

Olsalazine having the following formula has been used to treat ulcerative colitis.

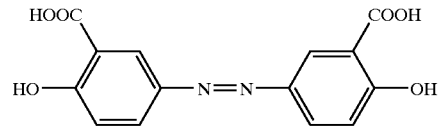

In addition to being relatively expensive to make, olsalazine may have adverse side effects including diarrhea.

It is known to use azathioprine (6-(1-methyl-4-nitoimidazol-5-ylthio)purine) in the treatment of inflammatory bowel disease. Azathioprine has the following chemical structure:

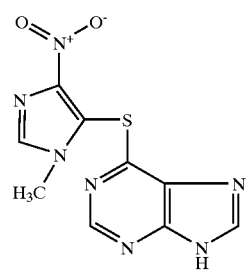

It is also known to use 6-mercaptopurine, a metabolite of azathioprine, to treat inflammatory bowel disease. 6-mercaptopurine has the following chemical structure:

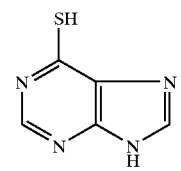

Methotrexate (L-4-amino-$N^{10}$-methylpteroyl-glutamic acid) has also been used to treat inflammatory bowel disease. Methotrexate has the following chemical structure:

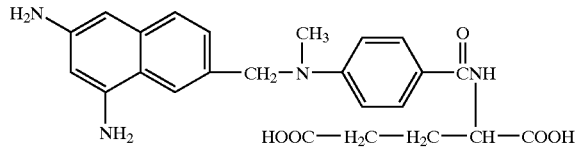

The polypeptide cyclosporine, which has traditionally been given to transplant patients to prevent organ rejection, has also been used to treat inflammatory bowel disease. The use of cyclosporine to treat IBD may be limited, however, by the various side effects associated with this medication. These side effects include high blood pressure, kidney damage, tremors, headaches, seizures, excessive hair growth, excessive gum growth, confusion, coma, and gout.

SUMMARY OF THE INVENTION

According to embodiments of the present invention, compounds are provided having the following formula:

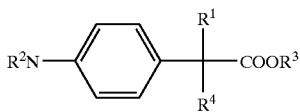

where $R^1$, $R^3$, and $R^4$ are independently hydrogen or $C_1$ to $C_4$ alkyl, and $R^2$ is:

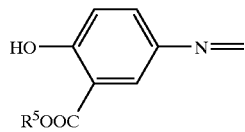

where $R^5$ is selected from the group consisting of hydrogen and $C_1$ to $C_4$ alkyl, or

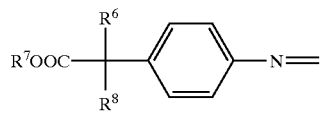

where $R^6$, $R^7$ and $R^8$ are independently hydrogen or $C_1$ to $C_4$ alkyl, as well as the esters or pharmaceutically acceptable salts of such compounds. Pharmaceutical compositions including compounds according to embodiments of the present invention are also provided, as are methods of treating inflammatory conditions with such compounds.

According to other embodiments of the present invention, methods of treating an inflammatory condition of the GI tract in a subject in need of such treatment include administering to the subject an effective amount of an active pharmaceutical ingredient that includes a compound of Formula II:

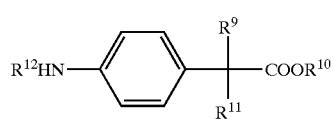

where $R^9$, $R^{10}$ and $R^{11}$ are independently selected from the group consisting of hydrogen and $C_1$ to $C_4$ alkyl; and $R^{12}$ is selected from the group consisting of hydrogen and —C(O)$R^{13}$, where $R^{13}$ is a $C_1$ to $C_6$ alkyl or an aryl group, or an ester or a pharmaceutically acceptable salt of such compound, in admixture with a solid or liquid pharmaceutical diluent or carrier. The active pharmaceutical ingredient may further comprise a compound of Formula III:

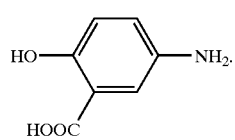

DETAILED DESCRIPTION OF THE PREFERRED EMBODIMENTS

The invention will now be described with respect to preferred embodiments described herein. It should be appreciated however that these embodiments are for the purpose of illustrating the invention, and are not to be construed as limiting the scope of the invention as defined by the claims.

As used herein, the term "inflammatory bowel disease" includes ulcerative colitis and Crohn's disease.

According to embodiments of the present invention, compounds are provided having the following formula:

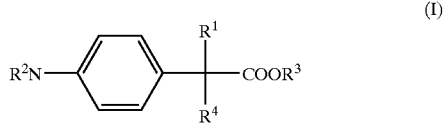

$R^1$, $R^3$, and $R^4$ are independently hydrogen or $C_1$ to $C_4$ alkyl. Preferably, $R^1$, $R^3$, and $R^4$ are independently selected from the group consisting of H, $CH_3$, $CH_2CH_3$, and $CH(CH_3)_2$. More preferably, $R^1$, $R^3$, and $R^4$ are H or $CH_3$. $R^2$ is:

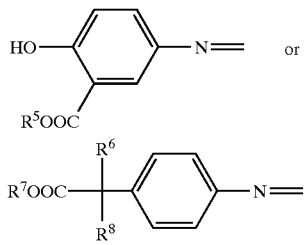

$R^5$ is selected from the group consisting of hydrogen and $C_1$ to $C_4$ alkyl. Preferably, $R^5$ is selected from the group consisting of H, $CH_3$, $CH_2CH_3$, and $CH(CH_3)_2$. More preferably, $R^5$ is H or $CH_3$ and, most preferably, $R^5$ is H.

$R^6$, $R^7$ and $R^8$ are independently hydrogen or $C_1$ to $C_4$ alkyl. Preferably, $R^6$, $R^7$ and $R^8$ are independently selected from the group consisting of H, $CH_3$, $CH_2CH_3$, and $CH(CH_3)_2$. More preferably, $R^6$, $R^7$ and $R^8$ are independently H or $CH_3$.

Figure 1:
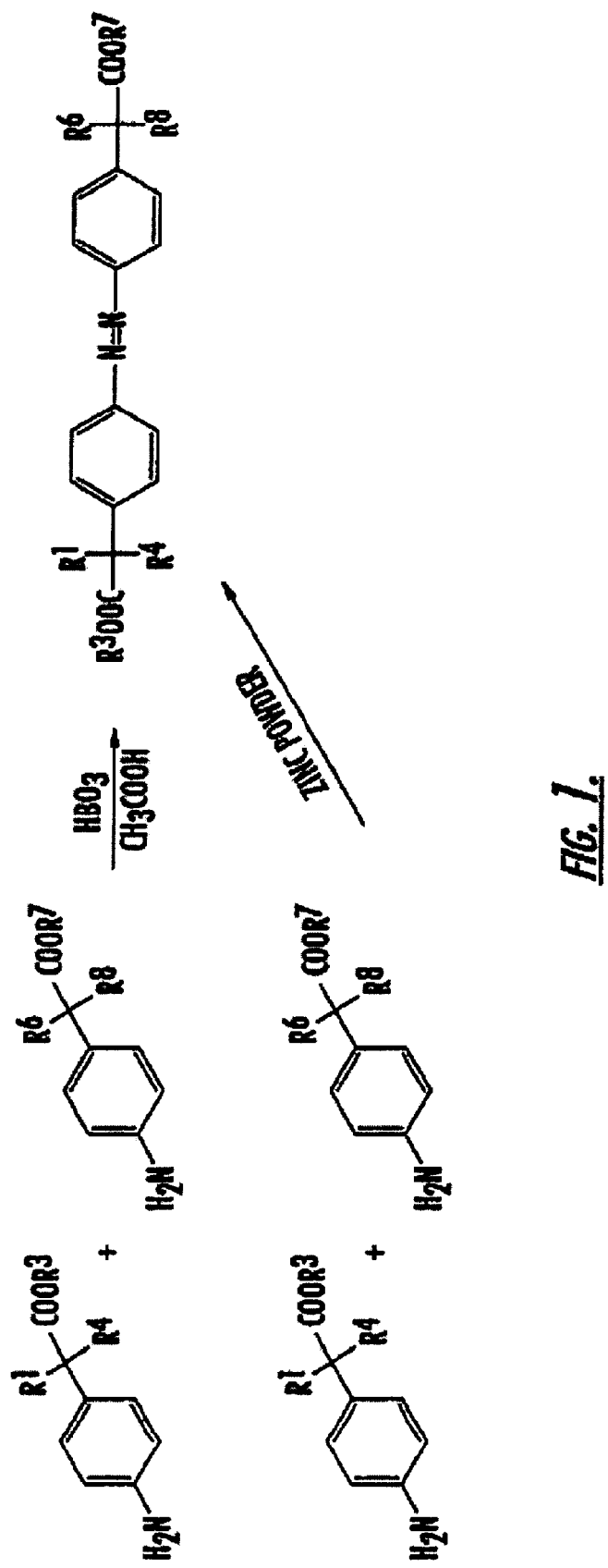
FIG. 1 illustrates embodiments of synthesis routes for compounds of the present invention.
Figure 2:
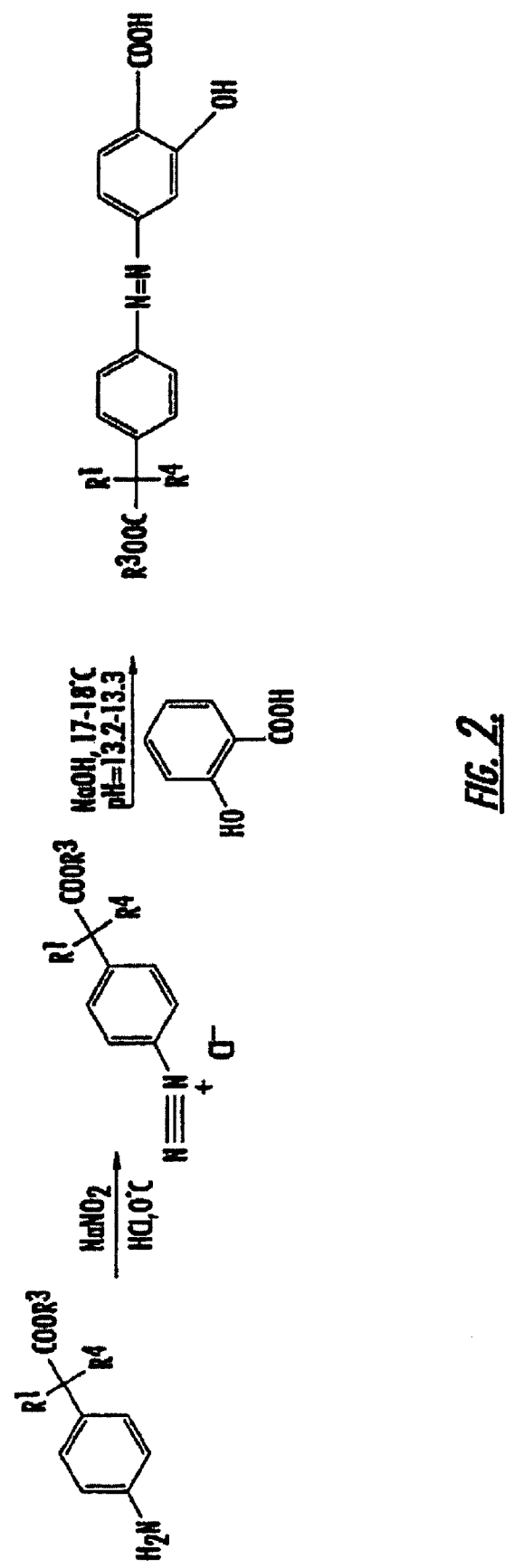
FIG. 2 illustrates embodiments of synthesis routes for compounds of the present invention.

The compounds of the present invention may be made using known starting materials and reagents. For example, embodiments of synthesis paths may be illustrated as shown in FIGS. 1 and 2.

Compounds of the present invention may be utilized for the prophylaxis or treatment of various diseases, particularly inflammatory conditions of the GI tract including, but not limited to, inflammatory conditions of the mouth such as mucositis, infectious diseases (e.g., viral, bacterial, and fungal diseases), and Crohn's disease; inflammatory conditions of the esophogas such as esophagitis, conditions resulting from chemical injury (e.g., lye ingestion), gastroesophageal reflux disease, bile acid reflux, Barrett's esophogas, Crohn's disease, and esophageal stricture; inflammatory conditions of the stomach such as gastritis (e.g., Helicobacter pylori, acid-peptic disease and atrophic gastritis), peptic ulcer disease, pre-cancerous lesions of the stomach, non-ulcer dyspepsia, and Crohn's disease; inflammatory conditions of the intestine such as celiac disease, Crohn's disease, bacterial overgrowth, peptic ulcer disease, and fissures of the intestine; inflammatory conditions of the colon such as Crohn's disease, ulcerative colitis, infectious colitis (e.g., pseudomembranous colitis such as clostridium difficile colitis, salmonella enteritis, shigella infections, yersiniosis, cryptosporidiosis, microsporidial infections, and viral infections), radiation-induced colitis, colitis in the immunocompromised host (e.g., typhlitis), precancerous conditions of the colon (e.g., dysplasia, inflammatory conditions of the bowel, and colonic polyps), proctitis, inflammation associated with hemorrhoids, proctalgia fugax, and rectal fissures; liver gallbladder and/or bilary tract conditions such as cholangitis, sclerosing cholangitis, primary bilary cirrhosis, and cholecystitis; and intestinal abscess. The compounds of the present invention may also be utilized in diagnosis of constituents, conditions, or disease states in biological systems or specimens, as well as for diagnostic purposes in non-physiological systems. Furthermore, the compounds of the present invention may have application in prophylaxis or treatment of condition(s) or disease state(s) in plant systems. By way of example, the active component of the conjugate may have insecticidal, herbicidal, fungicidal, and/or pesticidal efficacy amenable to usage in various plant systems.

In some embodiments, compounds of the present invention may breakdown in the intestinal tract to form the metabolic product of Formula IV:

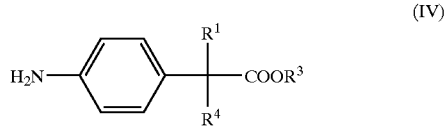

(IV)

where $R^1$, $R^3$ and $R^4$ are as described above with reference to Formula I, and the metabolic product of Formula V:

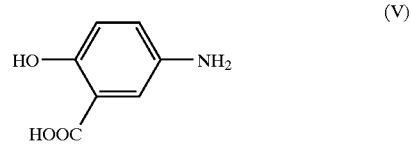

(V)

The metabolic product of Formula IV may possess anti-inflammatory activity and/or immunoregulatory activity. The metabolic product of Formula V may possess anti-inflammatory activity, and more particularly may provide inhibition of prostaglandin synthetase I & II.

In other embodiments, compounds of the present invention may breakdown in the intestinal tract to form the metabolic product of Formula IV and the metabolic product of Formula VI:

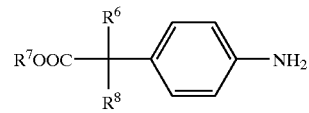

(VI)

where $R^6$, $R^7$ and $R^8$ are as described above with reference to Formula I. The metabolic product of Formula VI may possess anti-inflammatory activity and/or immunoregulatory activity. Accordingly, compounds of the present invention may provide immunoregulatory activity. Compounds of the present invention may also provide inhibition of prostaglandin synthetase I and II. Compounds of the present invention may be useful in treating various diseases, particularly ulcerative colitis, Crohn's disease and the like.

In therapeutic usage, the present invention contemplates a method of treating an animal subject having or latently susceptible to an intestinal condition(s) or disease state(s) and in need of treatment therefor, comprising administering to such animal an effective amount of a compound of the present invention that is therapeutically effective for said condition or disease state. Subjects to be treated by the compounds of the present invention include both human and non-human animal (e.g., bird, dog, cat, cow, horse) subjects, and are preferably mammalian subjects, and most preferably human subjects.

Depending on the specific condition or disease state to be combatted, animal subjects may be administered compounds of the present invention at any suitable therapeutically effective and safe dosage, as may readily be determined within the skill of the art and without undue experimentation. For example, compounds of the present invention may be administered at a dosage between about 0.1 and 100 mg/kg, preferably between about 5 and 90 mg/kg, and more preferably between about 10 and 80 mg/kg.

The compounds of the present invention may be administered per se as well as in the form of pharmaceutically acceptable esters, salts, and other physiologically functional derivatives thereof.

The present invention also contemplates pharmaceutical formulations, both for veterinary and for human medical use, which comprise as the active pharmaceutical ingredient one or more compound(s) of the present invention. In such pharmaceutical and medicament formulations, the active pharmaceutical ingredient preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and are preferably not unduly deleterious to the recipient thereof. The active pharmaceutical ingredient is provided in an amount effective to achieve the desired pharmacological effect, as described above, and in a quantity appropriate to achieve the desired daily dose.

The formulations include those suitable for parenteral as well as non-parenteral administration, and specific administration modalities include, but are not limited to, oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for oral and parenteral administration are preferred, with formulations suitable for oral administration most preferred.

When a compound of the present invention is utilized in a formulation comprising a liquid solution, the formulation advantageously may be administered orally or parenterally. When a compound of the present invention is employed in a liquid suspension formulation or as a powder in a biocompatible carrier formulation, the formulation may be advantageously administered orally, rectally, or bronchially.

When a compound of the present invention is utilized directly in the form of a powdered solid, the compound may advantageously be administered orally. Alternatively, it may be administered bronchially, via nebulization of the powder in a carrier gas, to form a gaseous dispersion of the powder that is inspired by the patient from a breathing circuit comprising a suitable nebulizer device.

The formulations comprising a compound of the present invention may conveniently be presented in unit dosage forms and may be prepared by any of the methods well known in the art of pharmacy. Such methods generally include the step of bringing a compound of the present invention into association with a carrier that constitutes one or more accessory ingredients. Typically, the formulations are prepared by uniformly and intimately bringing a compound of the present invention into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of a compound of the present invention as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding a compound of the present invention to a concentrated aqueous solution of a sugar, for example sucrose, to which may also be added any accessory ingredient(s). Such accessory ingredient(s) may include, for example, flavorings, suitable preservatives, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of a compound of the present invention, which preferably is isotonic with the blood of the recipient (e.g., physiological saline solution). Such formulations may include suspending agents and thickening agents or other microparticulate systems which are designed to target the compound to blood components or one or more organs. The formulations may be presented in unit-dose or multi-dose form.

Nasal spray formulations comprise purified aqueous solutions of a compound of the present invention with preservative agents and isotonic agents. Such formulations are preferably adjusted to a pH and isotonic state compatible with the nasal mucus membranes.

Formulations for rectal administration may be presented as a suppository with a suitable carrier such as cocoa butter, hydrogenated fats, or hydrogenated fatty carboxylic acid.

Ophthalmic formulations are prepared by a similar method to the nasal spray, except that the pH and isotonic factors are preferably adjusted to match that of the eye.

Topical formulations comprise a compound of the present invention dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

Accordingly, compounds according to the present invention may be utilized for the prophylaxis or treatment of various diseases, particularly diseases of the GI tract including, but not limited to, inflammatory bowel disease.

In still other embodiments of the present invention, methods of treating or preventing inflammatory bowel disease in a subject in need of such treatment or prevention include administering to the subject an effective amount of an active pharmaceutical ingredient that includes a compound of Formula II:

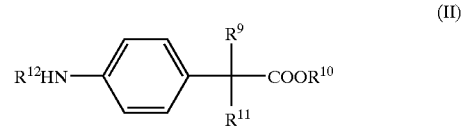

(II)

where $R^9$, $R^{10}$ and $R^{11}$ are independently selected from the group consisting of hydrogen and $C_1$ to $C_4$ alkyl; and $R^{12}$ is selected from the group consisting of hydrogen and —C(O)$R^{13}$, where $R^{13}$ is a $C_1$ to $C_6$ alkyl or an aryl group, or an ester or a pharmaceutically acceptable salt of such compound, in admixture with a pharmaceutical diluent or carrier.

The active pharmaceutical ingredient may further comprise one or more other medicaments including, but not limited to, anti-inflammatory agents such as mesalamine, sulfasalazine, balsalazide, and olsalazine; immunomodulators such as azathioprine, 6-mercaptorpurine, cyclosporine and methotrexate; steroidal compounds such as corticosteroids; and antibiotics such as metronidazole and cirpofloxacin. The active pharmaceutical ingredient preferably further comprises mesalamine, the compound of Formula III:

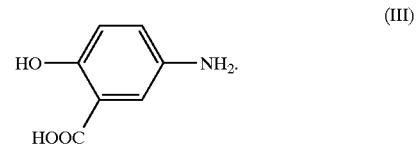

(III)

When the active pharmaceutical ingredient comprises compounds of Formula II and Formula III, the compound of Formula II is preferably from about 10 to 90 weight percent of the active pharmaceutical ingredient and is more preferably from about 40 to 60 weight percent of the active pharmaceutical ingredient. When the active pharmaceutical ingredient comprises compounds of Formula II and Formula III, the molar ratio of the compound of Formula I to the compound of Formula II is preferably between 1:10 and 10:1, and is more preferably between 1:2 and 2:1.

Subjects to be treated by methods according to these embodiments of the present invention include both human and non-human animal (e.g., bird, dog, cat, cow, horse) subjects, and are preferably mammalian subjects, and most preferably human subjects.

Depending on the specific condition or disease state to be combated, animal subjects may be administered the active pharmaceutical ingredient of the present invention at any suitable therapeutically effective and safe dosage, as may readily be determined within the skill of the art and without undue experimentation. For example, the active pharmaceutical ingredient of the present invention may be administered at a dosage between about 0.1 and 200 mg/kg, preferably between about 1 and 90 mg/kg, and more preferably between about 10 and 80 mg/kg.

The present invention will now be described with reference to the following examples. It should be appreciated that these examples are for the purposes of illustrating aspects of the present invention, and do not limit the scope of the invention as defined by the claims.

EXAMPLES

Examples 1 through 4

Synthesis of Compounds of the Present Invention

Melting points were taken on a Laboratory Devices Mel-Temp II capillary melting point apparatus and are uncorrected. $^1$HNMR spectra were obtained on a Varian Unity 600 MHz spectrometer. Chemical shifts ($\delta$) are reported as parts per million (ppm) relative to the internal standard tetramethylsilane. Ultraviolet and visible spectra were obtained with a Beckman DU 640i spectrophotometer. Infrared spectroscopy was obtained on a Nicolet Impact 410 and fast atom bombardment (FAB) mass spectroscopy data was obtained by M-Scan Inc. All reagents were used as received from Aldrich Chemical Co.

Examples 1 and 2

Synthesis of 5-[4-(1-Carboxy-Ethyl)-Phenylazo]-2-Hydroxy-Benzoic Acid

Example 1

2-(4-Amino-phenyl)-propionic acid

A 500-mL, oven dried, three-neck flask equipped with a stir bar, was charged with (R,S) 2-(4-nitrophenyl)propionic acid (5.00 g, 25.6 mmol), absolute ethyl alcohol (200 mL), and palladium (10 wt. % on activated carbon, 0.27 g, 2.56 mmol). A hydrogen environment was introduced into the flask and the mixture was then stirred at ambient temperature for 6 hours. The crude reaction mixture was filtered through Celite and the ethyl alcohol was removed under reduced pressure. The crude product was dried under vacuum overnight resulting in a light yellow solid (70% yield, 2.98 g): mp 125–129° C., $^1$H NMR (DMSO-d$_6$): $\delta$ 1.24 (3H, s), 1.26 (3H, s), 3.41 (1H, s), 3.43 (2H, s), 6.46 (2H, d, J=7.6 Hz), 6.91 (2H, d, J=7.6 Hz); IR (KBr) 2596, 2189, 1630, 1581, 1441, 1375, 1277, 1192, 1052, 876 cm$^{-1}$; FAB-MS (NBA) m/z 165 (M+H)$^+$.

Example 2

5-[4-(1-Carboxy-Ethyl)-Phenylazo]-2-Hydroxy-Benzoic Acid

As prepared in the above procedure, 2-(4-amino-phenyl)-propionic acid (3.90 g. 23.6 mmol) dissolved in an aqueous HCl solution (75 mL, 36.5-38.0% HCl in 8 mL H$_2$O) was placed in a 200-mL beaker and cooled to 0° C. in an ice bath. When the solution was stabilized at 0° C., sodium nitrite (1.79 g, 26.0 mmol) in water (2 mL) was added dropwise. The temperature was maintained at 0-5° C. and the resulting diazonium salt solution stirred for 15 min.

While the diazonium salt solution stirred, an 800-mL beaker fitted with a stir bar, thermometer, and pH probe (Orion model 420A with Orion semimicro pH probe) was charged with salicylic acid, sodium salt (11.3 g, 20.8 mmol) dissolved in sodium hydroxide (4.25 g, 106 mmol) and H$_2$O (100 mL). Using an ice bath, the salicylic acid solution was cooled to 17° C. and the diazonium salt solution was slowly added in 10 mL portions. Throughout the addition, the pH was maintained at 13.2-13.3 with the addition of aqueous sodium hydroxide, and the temperature was kept between 17-18° C. with the addition of ice. After the addition was complete, the resulting dark red solution was allowed to warm to ambient temperature and stirring was continued for 90 min. Upon acidification to pH 3.5 with concentrated HCl (~20 mL, 36.5-38%), a dark red solid precipitated and was collected by vacuum filtration.

The crude product (8.49 g, 27.0 mmol) was suspended in H$_2$O (300 mL) and heated at 70° C. for 30 min. to remove excess salicylic acid. The suspension was cooled to 50° C. and a solid was collected by suction filtration. The collected solid was then purified by flash chromatography (SiO$_2$: ethyl acetate/hexanes, 1:1). The crude product (2.50 g. 7.95 mmol) in DMF (~4.5 mL) was loaded and yellow colored fractions were collected, combined, and concentrated under reduced pressure. After drying under vacuum, the purified product was obtained as an orange solid in 55% yield (1.38 g): mp 147° C., $^1$H NMR (DMSO-d$_6$): $\delta$ 1.38 (3H, s), 1.39 (3H, s), 3.76 (1H, s), 3.78 (1H, s), 7.11 (1H, d,J=8.4 Hz), 7.46 (2H, d, J=7.8 Hz), 7.80 (2H, d, J=8.4 Hz), 8.03 (1H, d, J=9.0 Hz), 8.30 (1H, s); IR (KBr) 2973, 1921, 1708, 1652, 1577, 1477, 1339, 1289, 1226, 1164, 1101, 1013, 857, 663 cm$^{-1}$; UV-Vis (MeOH) $\lambda_{max}$=355 nm, $\epsilon$=23,700 mol$^{-1}$cm$^{-1}$ L; FAB-MS (NBA) m/z 313 (M)$^-$.

Example 3

Synthesis of 5-(4-Carboxymethyl-Phenylazo)-2-Hydroxy-Benzoic Acid [APAZA]

4-Aminophenylacetic acid (10.0 g, 66.2 mmol) dissolved in an aqueous HCl solution (20 mL, 36.5-38.0% HCl in 200 mL H$_2$O) was placed in a 500-mL beaker and cooled to 0° C. in an ice bath. When the solution was stabilized at 0° C., sodium nitrite (5.02 g, 72.8 mmol) in water (50 mL) was added slowly in 5 mL portions. The temperature was maintained at 0-5° C. and the resulting diazonium salt solution stirred for 15 min.

While the diazonium salt solution stirred, a 2L beaker fitted with a stir bar, thermometer, and pH probe (Orion model 420A with Orion semimicro pH probe) was charged with salicylic acid, sodium salt (31.8 g, 198 mmol) dissolved in sodium hydroxide (11.9 g, 230 mmol) and water (200 mL). Using an ice bath, the salicylic acid solution was cooled to 17° C. and the diazonium salt solution was slowly added in 25 mL portions. Throughout the addition, the pH was maintained at 13.2-13.3 with the addition of aqueous sodium hydroxide, and the temperature kept between 17-18° C. with the addition of ice. After the addition was complete, the resulting dark red solution was allowed to warm to ambient temperature and stirring was continued for an additional 30 min. Upon acidification to pH 3 with concentrated HCl (~50 mL, 36.5-38%), a brown solid precipitated and was collected by suction filtration.

The crude product was purified by flash chromatography (SiO$_2$: ethyl acetate/hexanes, 1:1). On a column packed with 70-230 mesh, 60 Å silica gel with BET surface area of ~500 m$^2$/g and pore volume of 0.75 cm$^3$/g, the crude product (11.5 g, 38.2 mmol) in DMF (~12 mL) was loaded. Fractions were collected and combined based on color. The first band was yellow in color and contained excess salicylic acid as well as traces of the desired product. The second band was orange and contained the desired product, and the third band was red and contained unknown impurities. All fractions were combined and concentrated under reduced pressure and dried under vacuum.

The purified product was obtained as an orange solid in 28% yield (2.75 g): mp 204° C.; $^1$H NMR (DMSO-d$_6$) δ 3.67 (2H, s), 7.11 (1H, d, J=9.0 Hz), 7.44 (2H, d, J=8.4 Hz), 7.79 (2H, d, J=8.4 Hz), 8.02 (1H, d of d, J=2.4 Hz, 9.0 Hz), 8.29 (1H, s); IR (KBr) 3098, 1696, 1614, 1458, 1345, 1195, 838 cm$^{-1}$; UV-Vis (MeOH) $\lambda_{max}$=350 nm, ε=25,700 mol$^{-1}$ cm$^{-1}$ L; positive FAB-MS (NBA) m/z 301 (M+H)$^+$, negative FAB-MS(NBA) m/z 299 (M)$^-$.

Example 4

Synthesis of 4-(4-Carboxymethyl-Phenylazo)-Phenylacetic Acid

4-Aminophenylacetic acid (3.75 g, 24.8 mmol) was suspended in water (75 mL) and concentrated hydrochloric acid (8 mL) was added. The solution was cooled to 0° C. in an ice bath with rapid stirring. Sodium nitrite (1.80 g, 26.1 mmol) in water (20 mL) was added dropwise to the 4-aminophenylacetic acid solution with rapid stirring. Care was taken to keep the temperature between 0-5° C. at all times, especially during the NaNO$_2$ addition. The reaction was stirred for an additional 20 min. In the meantime, phenylacetic acid (10.1 g, 74.4 mmol) was dissolved in an aqueous NaOH solution (4.50 g, 113 mmol NaOH in 100 mL H$_2$O). The solution was vigorously stirred at 17° C. and at pH 13.3. The diazonium salt solution was added dropwise to the phenylacetic acid solution. It is of utmost importance to keep the temperature of the phenylacetic acid solution between 17-18° C. and the pH between 13.2-13.3 at all times, especially during the diazonium salt addition. The temperature was regulated by the addition of ice and the pH regulated by the addition of 8 M NaOH. After addition was complete, the solution was allowed to warm to room temperature and stirred for an additional 30 min. The reaction mixture was suction filtered to remove any undissolved particulates or unwanted side products. The filtrate was acidified with aqueous HCl (10 mL conc. HCl in 20 mL H$_2$O) which produced a dark red precipitate. The precipitate was collected by suction filtration and washed several times with cold H$_2$O, until the filtrate was clear. The collected solid was air dried overnight to give the desired compound as a red solid in 37% yield: IR (KBr) 3030 (br), 1696, 1658, 1452, 1414, 1201, 850, 675 cm$^{-1}$ FABMS m/z 299 (M+H)$^+$, 320 (M+Na); $^1$H NMR (DMSO-d$_6$) δ 3.47 (s, 4H), 7.33 (4H, d, J=8.1 Hz), 7.84 (4H, d, J=8.4 Hz).

Example 5

Metabolism of APAZA Following Oral Delivery

The degradation of Apaza (5-(4-carboxymethyl-phenylazo)-2-hydroxy-benzoic acid), a compound of the present invention, and sulfasalazine (used as a control; not part of the present invention) and the generation of their metabolites when these compounds were orally dosed to rats were measured to be able to confirm that both Apaza and Sulfasalazine undergo bacterial azo reduction and yield their metabolites, 5-aminosalicylic acid (5-ASA) and sulfapyridine for sulfasalazine, 5-aminosalicylic acid (5-ASA) and 4-aminophenyl acetic acid (4-APAA) for Apaza.

This experiment was performed to confirm that an azo compound, Apaza, undergoes bacterial reduction process and yields its metabolites in in-vivo metabolism. The quantification of its metabolites was also carried out. Sulfasalazine, not part of the present invention, was used as a control since similar azo bond cleavage by bacteria occurs with it, which results in 5-aminosalicylic acid and sulfapyridine as its metabolites. Both Apaza and sulfasalzine were degraded and their metabolites were produced as expected.

For urine, the parent compounds and their metabolites were detected with day 1 collection only. The rest of the collections did not show any compounds. For feces, compounds were detectable up to day 2 collection.

Rats that were dosed with Apaza (rat 1, 2, and 3) showed Apaza, 4-APAA, actarit, and acetylated 5-ASA in urine. Rats with sulfasalazine dosage (rat 4, 5, and 6) showed sulfasalazine, sulfapyridine, and acetylated 5-ASA in urine. Only acetylated 5-ASA was detected in feces regardless of what compounds were given. 5-ASA was quickly converted to acetylated 5-ASA.

It is interesting to note that while sulfasalazine dosed rats produced their metabolites, 5-ASA (acetylated 5-ASA in this case) and sulfapyridine, in 1:1 ratio, rats with Apaza dosage produced 7 to 10 times more of 4-APAA than acetylated 5-ASA.

It is believed that the majority of the ingested sulfasalazine travels down the small intestine to the colon and undergoes bacterial azo reduction to liberate sulfapyridine and 5-ASA molecules. The results from this study confirm this belief and show that Apaza undergoes a similar bacterial azo reduction.

A total of 8 rats were used for the experiment and methylcellulose was used as a vehicle. The dosage amount was 100 mg/kg per rat. Three rats were dosed with Apaza and the other three rats were dosed with sulfasalazine. Two rats were used as a control and dosed with methylcellulose. Both urine and feces were collected over 4 days and analyzed by HPLC.

Urine was collected each day and 300 μL of aliquot from each sample was centrifuged for 10 minutes at 5000 g. 80 μL of supernatant was injected for analysis. Feces was also collected each day and homogenized with 1:1 mixture of water and acetonitrile. This mixture was then centrifuged for 20 minutes at 5000 g. 80 μL of supernatant was injected for analysis.

A Waters 2690 HPLC was used for sample analysis as follows: Mobile phase programming: Gradient

| Mobile phase: | A = Water + 0.1% TFA |
| --- | --- |
| | B = Acetonitrile + 0.1% TFA |
| Flow rate: | 1 mL/min. |
| Column: | Phenomenex Max RP, 80 Å, 4.6 mm × 250 mm |
| PDA settings: | Collected spectrum: 210–400 nm |
| | Extracted chromatogram: 280 and/or other |
| Run time/sample: | Approximately 50 mm. |

| Time | Flow (mL/minute) | % Mobile Phase A | % Mobile Phase B |
| --- | --- | --- | --- |
| — | 1 | 100 | 0 |
| 40 | 1 | 50 | 50 |
| 43 | 1 | 5 | 95 |
| 44 | 1 | 95 | 5 |
| 50 | 1 | 95 | 5 |

5-ASA was quickly converted to acetylated 5-ASA. The same amount of acetylated 5-ASA was generated from both Apaza and sulfasalazine in urine. Acetylated 5-ASA and sulfapyridine were produced in 1:1 ratio from sulfasalazine dosed rat urine. Approximately 7 to 10 times more of 4-APAA was produced than acetylated 5-ASA from Apaza dosed rat urine. Only acetylated 5-ASA was detected from feces regardless of dosed compound. More acetylated 5-ASA was detected in feces than urine.

Day 1

Apaza Dosed

| Urine | Total Dosage (mg) | Apaza (mg) | 4APAA (mg) | Actarit (mg) | Acetylated 5ASA (mg) |
|---|---|---|---|---|---|
| Rat 1 | 22.0 | 0.48 | 3.456 | 0.0717 | 0.299 |
| Rat 2 | 23.5 | 0.3546 | 3.177 | | 0.422 |
| Rat 3 | 22.5 | 0.4707 | 4.674 | | 0.298 |

Sulfasalazine Dosed

| | Total Dosage (mg) | Sulfasalazine (mg) | Sulfapyridine (mg) | Acetylated 5ASA (mg) |
|---|---|---|---|---|
| Rat 4 | 21 | 0.00882 | 0.337 | 0.288 |
| Rat 5 | 22.5 | 0.01279 | 0.305 | 0.328 |
| Rat 6 | 21 | 0.01092 | 0.41 | 0.39 |

| Stool | Total Dosage (mg) | Acetylated 5ASA (mg) |
|---|---|---|

Apaza Dosed

| | | |
|---|---|---|
| Rat 1 | 22 | 1.9254 |
| Rat 2 | 23.5 | 1.9519 |
| Rat 3 | 22.5 | 1.2437 |

Sulfasalazine Dosed

| | | |
|---|---|---|
| Rat 4 | 21 | 1.2158 |
| Rat 5 | 22.5 | 1.3708 |
| Rat 6 | 21 | 0.9033 |

Day 2

| Stool | Total Dosage (mg) | Acetylated 5ASA (mg) |
|---|---|---|

Apaza Dosed

| | | |
|---|---|---|
| Rat 1 | 22 | 0.2562 |
| Rat 2 | 23.5 | 0.7755 |
| Rat 3 | 22.5 | 0.1827 |

Sulfasalazine Dosed

| | | |
|---|---|---|
| Rat 4 | 21 | 0.2 |
| Rat 5 | 22.5 | 0.2584 |
| Rat 6 | 21 | 0.1458 |

Example 6

Biological Effects of Compounds of the Present Invention

The purpose of this study was to histologically evaluate and compare the effects of three different active pharmaceutical ingredients administered intrarectally (twice daily for four days) to male Lewis rats following intrarectal administration of dinitrobenzene sulfonic acid (DNBS). DNBS induced colitis in rats according to an established experimental model (Richard et al., 2000; Bertran et al., 1996; Blau et al., 2000; Kimura et al., 1998; Hogaboam et al., 1996). SHAM and DNBS groups served as negative and positive controls, respectively. The distribution of animals to each group is presented in Table 1:

TABLE 1

| GROUP | NUMBER OF ANIMALS |
|---|---|
| SHAM | 6 |
| DNBS | 5 |
| 5-ASA | 6 |
| 4-APAA | 6 |
| Mixture of 5-ASA and 4-APAA | 4 |

Materials And Methods

Trimmed specimens of colon from 27 male rats were tested, including microtoming, and hematoxylin and eosin staining. The resulting 27 slides (1 transverse section per slide) were examined microscopically. Except for one rat from the SHAM group and one rat from the DNBS group, all slides had their labels taped over to facilitate blind reading. Lesions were graded on a scale of 1-5 (1=minimal; 2=mild; 3=moderate; 4=moderately-severe; 5=severe).

Results

The principal histomorphologic change observed in the colon sections of all rats treated with DNBS (regardless of any additional treatment) was partial to full-thickness, full-length, coagulative-type necrosis. Necrosis was not observed in the saline/methylcellulose treated rats (SHAM group). In all cases, necrotic areas were characterized by a dramatic loss of cellular detail and staining affinity; in such areas only "ghost" outlines of the colonic architecture remained. Occasionally, segmental collapse or "dropout" of an intestinal tissue layer was evident. Necrotic tissues were heavily invaded by mixed types of bacteria. In sections that were not completely necrotic, the pattern of necrosis tended to be laminar, typically affecting the mucosa and submucosa while sparing portions of the muscularis externa and/or aciventitia (serosa and adjacent mesentery). In these sections, a dense zone of karyorrhectic neutrophils divided the necrotic inner layers from the less affected outer layers. Fibrinoid necrotizing vasculitis of submucosal blood vessels was observed in all DNBS-treated rats. Vasculitis was observed in both necrotic and non-necrotic regions, often accompanied by thrombosis (fibrinous, fibrinocellular, and/or bacterial thrombi), and minimal to moderate submucosal hemorrhage (with or without fibrin accumulation). Some hemorrhagic sites contained pigment-laden macrophages (siderophages—not separately diagnosed). In all sections from DNBS-treated rats, the serosa and adjoining mesentery were expanded by mild to moderately severe fibrovascular proliferation (early granulation tissue). Sections from two rats (#4 and #11, Mixture of 5-ASA and 4-APAA group), each contained a single, short, sharply demarcated segment of non-necrotic, non-ulcerated mucosa. Changes within these comparatively unaffected mucosal segments were limited to minimal to mild crypt epithelial hyperplasia, minimal crypt dilation, and minimal neutrophilic infiltration.

Severity scoring of colonic necrosis was based upon the degree of tissue involvement; however, grade 5 (severe) was reserved for lesions in which necrosis resulted in extensive tissue loss. Because the pattern of necrosis often varied from section to section, the individual intestinal layers were scored separately. Generally, the average severity scores for necrosis were comparable among the four groups of DNBS-treated rats (Table 2). The average score for mucosal necrosis in the Mixture of 5-ASA and 4-APAA group was lower than scores in the other groups of DNBS-treated rats due to the spared areas of mucosa in two animals from the Mixture of 5-ASA and 4-APAA group.

TABLE 2

Average Tissue Necrosis Scores

| Group | SHAM | DNBS | 5-ASA | 4-APAA | Mixture 5-ASA & 4-APAA |
|---|---|---|---|---|---|
| No. Animals | (6) | (5) | (6) | (6) | (4) |
| Mucosa | 0.00 | 4.20 | 4.50 | 4.33 | 3.50 |
| Submucosa | 0.00 | 4.20 | 4.17 | 4.00 | 4.25 |
| Muscularis | 0.00 | 3.60 | 3.5 | 3.17 | 3.00 |
| Adventitia | 0.00 | 1.40 | 1.67 | 1.67 | 1.50 |

Summary

The principal histomorphologic change observed in the colon sections of all rats treated with DNBS (regardless of any additional treatment) was partial to full-thickness, full-length, coagulative-type necrosis. Associated changes included massive bacterial invasion of the necrotic tissue, fibrinoid necrotizing vasculitis with thrombosis and hemorrhage, and heavy neutrophilic infiltration. Necrosis was not observed in the saline/methylcellulose-treated rats (SHAM group). The severity (extent) of necrosis was comparable among the four groups of DNBS-treated rats (DNBS, 5-ASA, 4-APAA, and Mixture of 5-ASA and 4-APAA), except that single segments of mucosa were comparatively spared in 2/4 rats from the Mixture of 5-ASA and 4-APAA group.

Example 7

Anti-inflammatory Activity of Drug Mixture

Dinitrobenzene sulfonic acid (DNBS) colitis was induced (no ether anesthesia) in 4 groups of 6 Lewis rats each. One DNBS group was dosed with vehicle (0.7% methyl cellulose) as well as an additional sham group of 6 animals that received a saline enema instead of DNBS. Intrarectal (ir) dosing was performed in conscious animals b.i.d. for 4 days. Drug treatments were as follows:

5-aminosalicylic acid (5-ASA): 50 mg/kg 4-aminophenylacetic acid (4-APAA): 49.5 mg/kg (equimolar to 5-ASA)

Mixture: 5-ASA+4-APAA: 50 mg/kg+49.5 mg/kg

Drugs were suspended in the above mentioned vehicle and staff blinded to drug groups. Daily weights and diarrhea scores were recorded. On the 5th day post-irritant rats were sacrificed, laparotomies performed and scored for intestinal adhesions and strictures; colectomized and colon weights recorded, colons opened longitudinally and inflammation/ulcerations scored.

Figure 3:
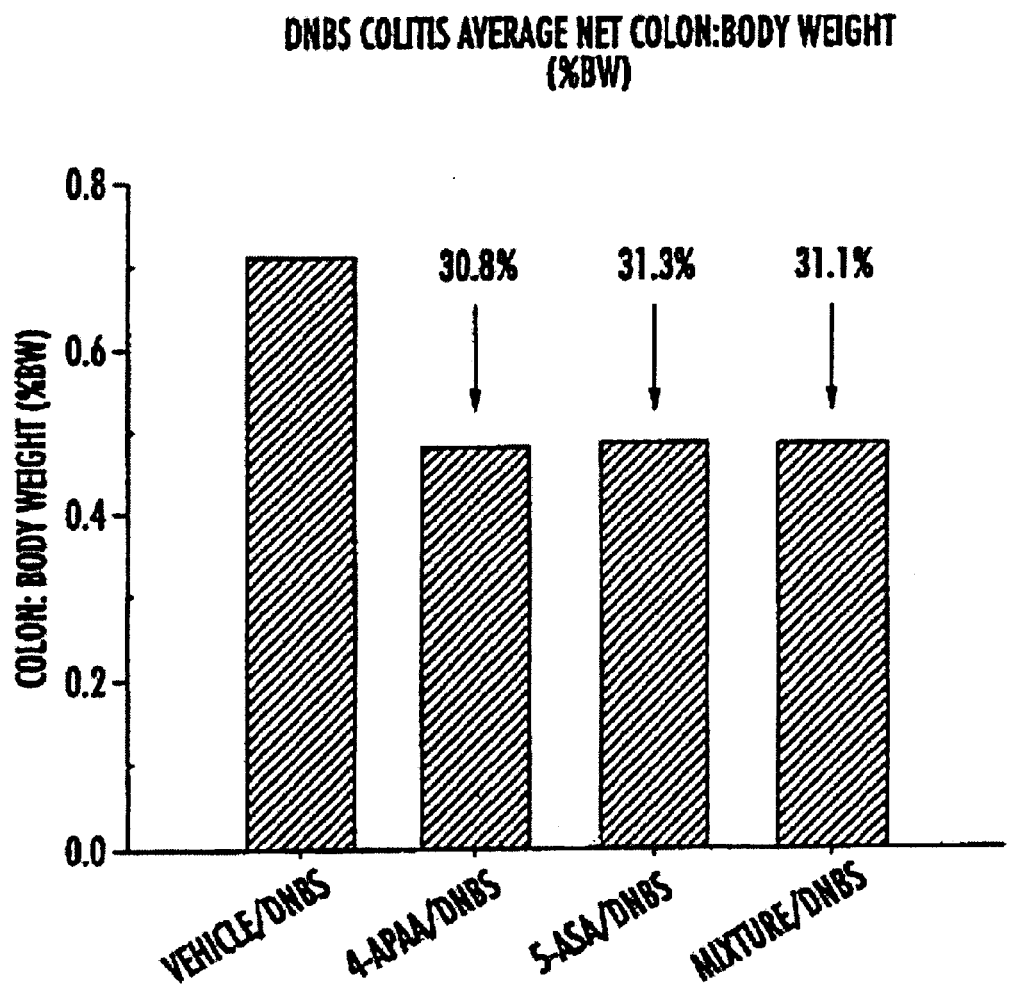
FIG. 3 illustrates the average reduction in colon:body weight [% BW] utilizing embodiments of the present invention (4-APAA/DNBS and Mixture/DNBS) in comparison with results achieved by the prior art (5-ASA/DNBS) and control (Vehicle/DNBS).
Figure 4:
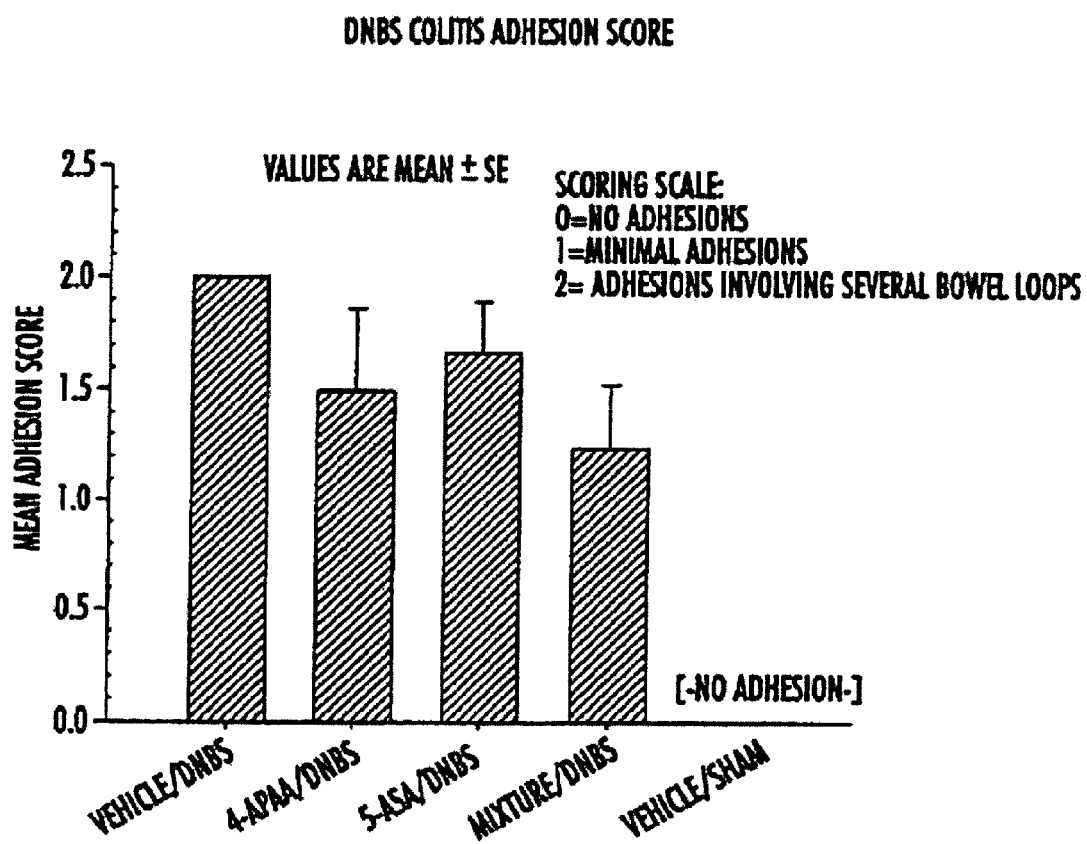
FIG. 4 illustrates DNBS colitis adhesion scores achieved utilizing embodiments of the present invention (4-APAA/DNBS and Mixture/DNBS) in comparison with results achieved by the prior art (5-ASA/DNBS) and control (Vehicle/DNBS and Vehicle/Sham).

Results illustrated in FIGS. 3 and 4 indicated that 5-ASA, 4-APAA, and the mixture produce similar anti-inflammatory activity (~31% reduction in colon:body weight [% BW]). The severity of inflammation approached maximum. It is possible that the severity could be titrated by reduction of the DNBS dose and a small study was performed to test this hypothesis. It is possible that with a milder insult there may be evidence of greater separation of treatment effects.

DNBS colitis was induced in 6 Lewis rats (3 at 30 and 3 at 15 mg/rat DNBS) and allowed to develop for 5 days with no treatment in order to citrate the severity of inflammation. Diarrhea was noted on days 1-4 and the rats were sacrificed on day 5, scored, and colon:body weight determined. Results indicate that 15 mg/rat DNBS produces milder but inconsistent inflammation compared to 30 mg. The 30 mg/kg DNBS result was consistent with that seen previously.

The foregoing is illustrative of the present invention, and is not to be construed as limiting thereof. The invention is defined by the following claims, with equivalents of the claims to be included therein.

That which is claimed is:

1. A method of treating an inflammatory condition of the gastrointestinal tract in a subject in need of such treatment comprising administering to the subject an effective amount of an active pharmaceutical ingredient consisting essentially of a compound of Formula II:

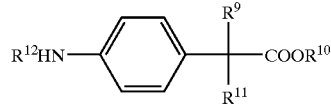

(II)

where $R^9$, $R^{10}$ and $R^{11}$ are independently selected from the group consisting of hydrogen and $C_1$ to $C_4$ alkyl; and $R^{12}$ is selected from the group consisting of hydrogen and —C(O)$R^{13}$, where $R^{13}$ is a $C_1$ to $C_6$ alkyl or an aryl group;

or an ester or a pharmaceutically acceptable salt of such compound, in admixture with pharmaceutical diluent or carrier.

2. The method according to claim 1, wherein $R^9$, $R^{10}$, and $R^{11}$ are independently selected from the group consisting of H, $CH_3$, $CH_2CH_3$, and $CH(CH_3)_2$.

3. The method according to claim 1, wherein $R^9$, $R^{10}$, and $R^{11}$ are independently selected from the group consisting of H and $CH_3$.

4. The method according to claim 1, wherein $R^{12}$ is hydrogen.

5. The method according to claim 1, wherein the compound of Formula II is 4-aminophenylacetic acid.

6. The method according to claim 1, wherein the inflammatory condition of the gastrointestinal tract is ulcerative colitis.

7. The method according to claim 1, wherein the inflammatory condition of the gastrointestinal tract is Crohn's disease.

8. The method according to claim 1, wherein the administering of an effective amount of the active pharmaceutical ingredient comprises orally administering to the subject an effective amount of the active pharmaceutical ingredient.

9. The method according to claim 1, wherein the administering of an effective amount of the active pharmaceutical ingredient comprises rectally administering to the subject an effective amount of the active pharmaceutical ingredient.

10. A method of treating an inflammatory condition of the gastrointestinal tract in a subject in need of such treatment comprising administering to the subject an effective amount of an active pharmaceutical ingredient comprising (a) 4-aminophenylacetic acid and/or esters or pharmaceutically acceptable salts thereof and (b) 5-aminosalicylic acid and/or esters or pharmaceutically acceptable salts thereof.

11. The method according to claim 10, wherein the 4-aminophenylacetic acid is from about 10 to 90 weight percent of the active pharmaceutical ingredient.

12. The method according to claim 10, wherein the molar ratio of the 4-aminophenylacetic acid to the 5-aminosalicylic acid is between about 1:10 and 10:1.

13. The method according to claim 10, wherein the inflammatory condition of the gastrointestinal tract is ulcerative colitis.

14. The method according to claim 10, wherein the inflammatory condition of the gastrointestinal tract is Crohn's disease.

15. The method according to claim 10, wherein the administering of an effective amount of the active pharmaceutical ingredient comprises orally administering to the subject an effective amount of the active pharmaceutical ingredient.

16. The method according to claim 10, wherein the administering of an effective amount of the active pharmaceutical ingredient comprises rectally administering to the subject an effective amount of the active pharmaceutical ingredient.

* * * * *